(12) United States Patent
Krapp et al.

(10) Patent No.: US 8,212,054 B2
(45) Date of Patent: Jul. 3, 2012

(54) CRYSTALLINE COMPLEXES OF PENDIMETHALIN AND METAZACHLOR

(75) Inventors: Michael Krapp, Altrip (DE); Wolfgang Gregori, Ludwigshafen (DE); Heidi Emilia Saxell, Carlsberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/123,991

(22) PCT Filed: Oct. 13, 2009

(86) PCT No.: PCT/EP2009/063328
§ 371 (c)(1),
(2), (4) Date: Apr. 13, 2011

(87) PCT Pub. No.: WO2010/043607
PCT Pub. Date: Apr. 22, 2010

(65) Prior Publication Data
US 2011/0201502 A1 Aug. 18, 2011

(30) Foreign Application Priority Data

Oct. 14, 2008 (EP) .................................. 08166600

(51) Int. Cl.
C07D 231/12 (2006.01)
A01N 43/56 (2006.01)
(52) U.S. Cl. .................................. 548/375.1; 514/406
(58) Field of Classification Search ............... 548/375.1; 514/406
See application file for complete search history.

(56) References Cited

U.S. PATENT DOCUMENTS

| 4,874,425 A | 10/1989 | Kimpara et al. |
| 5,624,884 A * | 4/1997 | Morgan et al. ................ 504/148 |
| 6,022,501 A | 2/2000 | Dexter et al. |

FOREIGN PATENT DOCUMENTS

| CA | 2 022 133 | 1/1991 |
| EP | 0 249 770 | 12/1987 |
| EP | 0 411 408 | 2/1991 |
| EP | 0411408 | * 2/1991 |
| EP | 0 823 993 | 2/1998 |
| WO | WO 02/15690 | 2/2002 |

OTHER PUBLICATIONS

International Search Report prepared in International Application No. PCT/EP2009/063328, filed Oct. 13, 2009.
International Preliminary Report on Patentability from corresponding International Application No. PCT/EP2009/063328, filed Oct. 13, 2009.
Bowerman, P., "Efficacy and tolerance of newly planted trees to herbicides", Database CA [Oline], Chemical Abstracts Service, Columbus, Ohio, US, XP002614221, retrieved from STN, Database accession No. 122:25789, (1994), Search Report Abstract Only.

(Continued)

*Primary Examiner* — Kamal Saeed
*Assistant Examiner* — Janet L Coppins
(74) *Attorney, Agent, or Firm* — Brinks Hofer Gilson & Lione (57) ABSTRACT

The present invention relates to crystalline complexes of pendimethalin and metazachlor. It also relates to agriculturally useful compositions of the complexes.

16 Claims, 2 Drawing Sheets

OTHER PUBLICATIONS

Clay, D.V. et al, "Effect of herbicide mixtures applied to newly-planted poplar and willow coppice.", Database CA [Online], Chemical Abstracts Service, Columbus, Ohio, US, XP002614222, retrieved from STN, Database accession No. 121:101851, (1993), Search Report Abstract Only.

Griesse, U.J. et al, "The crystal polymorphs of metazachlor", Database CA [Online], Chemical Abstracts Service, Columbus, Ohio, US, XP002614220, retrieved from STN, Database accession No. 141:407201, (2004), Search Report Abstract Only.

* cited by examiner

CRYSTALLINE COMPLEXES OF PENDIMETHALIN AND METAZACHLOR

This application is a National Stage application of International Application No. PCT/EP2009/063328, filed Oct. 13, 2009, the entire contents of which is hereby incorporated herein by reference. This application also claims priority under 35 U.S.C. §119 to European Patent Application No. 08166600.0, filed Oct. 14, 2008, the entire contents of which is hereby incorporated herein by reference.

The present invention relates to crystalline complexes of pendimethalin and metazachlor. It also relates to agriculturally useful compositions of these complexes.

Agriculturally active organic compounds such as fungicides, herbicides and insecticides or acaricides are usually marketed as liquid or solid formulations which comprise one or more agriculturally active organic compounds and suitable formulation additives. For several reasons, formulation types are preferred, wherein the agriculturally active organic compound is present in the solid state, examples including solid formulations such as dusts, powders or granules and liquid formulations such as suspension concentrates, i.e. aqueous compositions containing the active organic compound as fine particles which are dispersed in the aqueous medium. Suspension concentrates have the desirable characteristics of a liquid that may be poured or pumped and which can easily be diluted with water to the desired concentration required for application. In contrast to emulsion concentrates the suspension concentrates have the added advantage of not requiring the use of water-immiscible organic solvents.

For purposes of such solid state formulations the agriculturally active organic compounds should be crystalline materials having a sufficiently high melting point. Unfortunately, a large number of these organic compounds are amorphous materials and/or have low melting points resulting in processing difficulties, formulation instabilities and application unreliability due to caking and settling of the fine particles. These problems are pronounced in case of the herbicide pendimethalin (common name for N-(1-ethyl propyl)-2,6-dinitro-3,4-dimethylanilin) as pendimethalin has a low melting point of 55-57° C. and furthermore suffers a melting point depression, even in the presence of small amounts of impurities or formulation additives.

A further problem associated with formulations of pendimethalin results from the tendency of pendimethalin to form large crystals upon aging resulting in an increased settling of pendimethalin particles and thus in an instability, difficulty in processing and unreliability of usage. These problems become most serious when storing aqueous suspension concentrates of pendimethalin at temperatures above 35° C. and especially above 40° C.

U.S. Pat. No. 4,874,425 discloses an aqueous concentrate composition of pendimethalin which comprises sodium or calcium lignin sulfonate as stabilizer.

EP 249 770 discloses stable suspension concentrates of pendimethalin which are prepared by emulsifying molten pendimethalin in hot water, adding a surfactant and antifoaming agents to provide a droplet size of the pendimethalin droplets of about 2 to 10 µm and cooling the hot emulsion to ambient temperature while agitating.

EP-A-823 993 teaches an aqueous microcapsule composition which contains pendimethalin being microencapsulated by a pH-sensitive polymeric material.

Another approach for improving the applicability of low-melting organic agents for aqueous formulations is to provide crystalline complexes of these agents that have higher melting points and thus may allow for stable aqueous suspension of its fine particles.

Crystalline complexes of organic compounds, also termed as co-crystals are multi-component crystals or crystalline materials that consist of at least two different organic compounds which are usually solid at 25° C. or at least a non-volatile oil (vapour pressure less than 1 mbar at 25° C.). In the crystalline complexes (or co-crystals) at least two different organic compounds form a crystalline material having a defined crystal structure, i.e. the at least two organic compounds have a defined relative spatial arrangement within the crystal structure.

In the co-crystals, at least two different compounds interact by non-covalent bonding such as hydrogen bonds and, possibly, other non-covalent intermolecular forces, including π-stacking, dipole-dipole interactions and van der Waals interactions.

Although the packing in the crystalline lattice cannot be designed or predicted, several supramolecular synthons could successfully recognized in co-crystals. The term "supramolecular synthon" has to be understood as an entity of usually two compounds that are bonded together via non-covalent interactions. In co-crystals these synthons further pack in the crystalline lattice to form a molecular crystal. Molecular recognition is one condition of the formation of the synthon. However, the co-crystal must also be energetically favourable, i.e. an energy win in the formation of the co-crystal is also required, as molecules typically can pack very efficiently as crystals of pure components thereby hindering the co-crystal formation.

In co-crystals one of the organic compounds may serve as a co-crystal former, i.e. a compound which itself easily forms a crystalline material and which is capable of forming co-crystals with other organic compounds which themselves may not necessarily form a crystalline phase.

Crystalline complexes of active pharmaceutical compounds have been described in the art on various occasions, e.g. in US2003/224006, WO03/074474, WO2005/089511, EP1608339, EP1631260 and WO2006/007448.

Metazachlor (common name for 2-chloro-N-(2,6-dimethylphenyl)-N-(1H-pyrazol-1-ylmethyl)acetamide) is a is a well known crystalline herbicide of the formula which exists in three different polymorphic forms. The thermodynamically most stable one is the monoclinic form which is known from EP 411408. The polymorphs are further described in U. J. Griesser, D. Weigand, J. M. Rollinger, M. Haddow, E. Gstrein, *J. Therm. Anal. Calorim.*, 77 (2004) 511 and D. Weigand, Ph.D. thesis, Innsbruck, 2001. The reported melting points are in the range of 76° C. to 83° C. Metazachlor belongs to the groups of the chloroacetanilide and the pyrazole herbicides.

Pendimethalin is an established crystalline herbicide of the formula which according to Stockton et al. occurs in triclinic and monoclinic crystal structures (cf. G. W. Stockton, R. Godfrey, P. Hitchcock, R. Mendelsohn, P. C. Mowery, S. Rajan, A. F. Walker, *J. Chem. Soc., Perkin Trans.* 2, 1998, 2061). The reported melting points are in the range of 57° C. and 55° C., respectively. Pendimethalin belongs to the group of the dinitroanilin herbicides.

The inventors of the present invention surprisingly found that metazachlor is a suitable co-crystal partner that forms crystalline complexes with pendimethalin. Thus, the present invention relates to crystalline complexes comprising pendimethalin and metazachlor and in particular consisting of pendimethalin and metazachlor.

The crystalline complexes according to the present invention have a defined crystal structure and have a reasonable high melting point which facilitates the incorporation of such complexes into solid or liquid formulations wherein the active material is present in the solid state. Moreover, the formulations of such crystalline complexes show increased stability, in particular in comparison with formulations containing a mixture of pendimethalin and metazachlor as individual solid compounds.

It is presumed that the formation of the crystalline complexes according to the present invention results from the ability of pendimethalin and metazachlor to form a energetically favourable crystalline lattice wherein they are arranged to each other in a defined relative spatial order, so that the association of the two molecules represents the supramolecular synthon of the crystal structure.

In the crystalline complexes according to the present invention, the molar ratio of metazachlor and pendimethalin is generally in the range of 0.5:1 to 2:1 and is preferably from 0.8:1 to 1.25:1. In particular, the molar ratio is from 0.9:1 to 1.1:1 and specifically about 1:1. However, deviations are possible, though they will generally not exceed 20 mol-% and preferably not exceed 10 mol-%.

The crystalline complexes can be distinguished from simple mixtures of crystalline metazachlor and crystalline pendimethalin by standard analytical means used for the analysis of crystalline material, including X-ray powder diffractometry (PXRD) and thermochemical analysis such as thermogravimetry (TGA) and differential scanning calorimetry (DSC). Relative amounts of metazachlor and pendimethalin can be determined e.g. by HPLC or by $^1$H-NMR-spectroscopy.

The crystalline complex of metazachlor and pendimethalin shows an X-ray powder diffractogram at 25° C. (Cu-radiation, 1.5406 Å); wherein the characteristic reflexes of the pure compounds are missing. In particular, the crystalline complex of metazachlor and pendimethalin shows at least 4, preferably at least 6, in particular at least 8 and more preferably all of the following reflexes, given in the following table 1 as 2θ values or as lattice spacings d:

TABLE 1

PXRD of the crystalline complex of metazachlor and pendimethalin (25° C., Cu-radiation, 1.5406 Å)

| 2θ values | d [Å] |
|---|---|
| 6.40 ± 0.2 | 13.89 ± 0.4 |
| 7.06 ± 0.2 | 12.54 ± 0.3 |
| 7.36 ± 0.2 | 12.00 ± 0.3 |
| 11.82 ± 0.2 | 7.48 ± 0.1 |
| 12.78 ± 0.2 | 6.93 ± 0.08 |
| 14.72 ± 0.2 | 6.01 ± 0.05 |
| 19.21 ± 0.2 | 4.62 ± 0.03 |
| 21.28 ± 0.2 | 4.17 ± 0.03 |
| 22.15 ± 0.2 | 4.01 ± 0.03 |

Studies of single crystals of the crystalline complex of metazachlor and pendimethalin show that the basic crystal structure is triclinic and has the space group P-1. The structure analysis reveals that the crystalline complex is a 1:1 mixture of metazachlor and pendimethalin with the asymmetric unit containing one molecule of metazachlor and pendimethalin, each. The spatial arrangement of the metazachlor and pendimethalin molecules in the crystal seems to be mainly driven by energetically favourable 3-dimensional packing as well as dipole-dipole interactions and weak H-bonding in between metazachlor and pendimethaline molecules. The characteristic data of the crystal structure of the complex are shown in table 2:

TABLE 2

Crystallographic data of the crystalline complex of metazachlor and pendimethalin

| Parameter | |
|---|---|
| Class | Triclinic |
| Space group | P-1 |
| a | 7.447(2) Å |
| b | 13.834(3) Å |
| c | 15.225(3) Å |
| α | 112.93(1)° |
| β | 98.06(1)° |
| γ | 97.96(1)° |
| Volume | 1397.9(2) Å$^3$ |
| Z | 4 |
| Density (calculated) | 1.328 g/Å$^3$ |
| R1, wR2 | 0.059, 0.126 | a, b, c = Length of the edges of the unit cell
α, β, γ = Angles of the unit cell
Z = Number of molecules in the unit cell The DSC-measurement of the crystalline complex of metazachlor and pendimethalin shows an endothermic melting peak with onset at 55-57° C. and peak maximum at 59-62° C. The melting point of the crystalline complex is thus similar to that of the known pendimethalin modifications and about 14 to 21° C. lower than the melting point of metazachlor.

The crystalline complexes of the present invention can be prepared by co-crystallizing metazachlor and pendimethalin from a solution or slurry or from a melt containing metazachlor and pendimethalin. Likewise, it is possible to prepare the crystalline complexes of the present invention by a process which comprises combining (or mixing, respectively) an aqueous suspension of pendimethalin with an aqueous suspension of metazachlor, preferably at an elevated temperature, e.g. above 30° C.

In a preferred embodiment of the process for preparing the crystalline complex of metazachlor and pendimethalin, the complex is obtained from a slurry of metazachlor and pendimethalin in an organic solvent or in particular from a slurry of metazachlor and pendimethalin in a mixture of water and organic solvent. Consequently, this method comprises suspending metazachlor and pendimethalin in an organic solvent or in a mixture of water and organic solvent (so called slurry process).

Preferred organic solvents or mixtures of water and organic solvent for the slurry process are those, where pendimethalin and metazachlor have a comparable solubility. Comparable solubility means that the solubilities of the individual compounds in the solvent or solvent system differ by a factor of not more than 20, in particular by a factor of not more than 10. It is, however, also possible to use a solvent or solvent system, wherein the solubilities of the individual compounds are not comparable. In this case, it might be preferable to use the compound having the higher solubility in the respective solvent or solvent system in excess.

Preferred organic solvents for the slurry process are those, which are at least partially water miscible, i.e. which have miscibility with water of at least 10% v/v, more preferably at least 20% v/v at room temperature, and mixtures thereof. Likewise preferred are mixtures of said at least partially water miscible solvents with organic solvents that have miscibility with water of less than 10% v/v at room temperature. Preferably the organic solvent comprises at least 80% v/v, based on the total amount of organic solvent, of the at least one at least partially water miscible organic solvent.

Suitable solvents having a water miscibility of at least 10% at room temperature include, but are not limited to:
1. $C_1$-$C_4$-Alkanols such as methanol, ethanol, n-propanol or isopropanol;
2. Amides, N-methylamides and N,N-dimethylamides of $C_1$-$C_3$-carboxylic acids such as formamide, dimethylformamide (DMF), acetamide and N,N-dimethylacetamide;
3. 5 or 6-membered lactames with a total of 7 carbon atoms such as pyrrolidone, N-methylpyrrolidone, N-ethylpyrrolidone, N-isopropylpyrrolidone, N-hydroxyethylpyrrolidone, piperidone, N-methylpiperidone, caprolactam, or N-methylcaprolactam;
4. Dimethylsulfoxid and sulfolane;
5. Ketones with 3 to 6 carbon atoms such as acetone, 2-butanone, cyclopentanone and cyclohexanone;
6. Acetonitrile or propionitrile;
7. 5- or 6-membered lactones such as γ-butyrolactone;
8. Polyols and polyetherols such as glycol, glycerin, dimethoxyethan, ethylendiglycol, ethylenglycolmonomethylether, etc;
9. Cyclic carbonates having 3 to 5 carbon atoms including propylene carbonate and ethylene carbonate; and
10. Dimethyl (poly)$C_2$-$C_3$-alkyleneglycol ethers such as dimethoxyethane, diethyleneglycoldimethylether, triethyleneglycoldimethylether, dipropyleneglycoldimethylether, low molecular weight polyethyleneglycoles and low molecular weight polypropyleneglycoles (MW≦400).

More preference is given to organic solvents of the group 1, and to their mixtures with water. In the mixtures with water the relative amount of organic solvent and water may vary from 2:1 to 1:200 (v/v), in particular from 1:5 to 1:100 (v/v).

The slurry process can by simply performed by suspending metazachlor and pendimethalin in the organic solvent or in a solvent/water mixture. The relative amounts of metazachlor, pendimethalin and solvent or solvent/water mixture will be chosen to obtain a suspension at the given temperature. Complete dissolution of pendimethalin and metazachlor should be avoided. In particular metazachlor and pendimethalin are suspended in an amount from 1 to 500 g, more preferably 10 to 400 g per litre of solvent or solvent/water mixture.

The relative molar amount of metazachlor and pendimethalin in the slurry process may vary from 1:100 to 100:1, preferably from 1:10 to 10:1, depending on the relative solublities of metazachlor and pendimethalin in the chosen solvent or solvent system. In solvent systems where the solubilities of the pure metazachlor and pendimethalin are comparable the preferred molar ratio is from 2:1 to 1:2, in particular from 1.5:1 to 1:1.5 and especially about 1:1 (i.e. from 1.1:1 to 1:1.1). An excess of pendimethalin will be used in solvent systems where pendimethalin has a higher solubility. This applies also vice versa with Metazachlor. If one of the components is in excess with regard to the stoichiometry of the crystalline complex, a mixture of the crystalline complex and the compound being in excess might be obtained, though an excess will usually remain dissolved in the mother liquor, in particular if the compound which is used in excess has a high solubility in the chosen solvent system. For formulation purposes, the presence of an excess of pendimethalin or metazachlor might be acceptable. In particular the presence of an excess of metazachlor does not cause stability problems. For preparing the pure crystalline complex, metazachlor and pendimethalin will be used in a relative molar amount which is close to the stoichiometry of the complex to be formed and which usually will not deviate more than 50 mol.-%, based on the stoichiometrically required amount.

The slurry process is usually performed at a temperature of at least 5° C., preferably at least 10° C. and in particular at least 20° C., e.g. from 5 to 80° C., preferably from 10 to 55° C., in particular from 20 to 40° C.

The time required for formation of the crystalline complex by the slurry process depends on the temperature, the type of solvent and is generally at least 2 h and frequently at least 6 h. In any case, complete conversion is achieved after one week, however, the complete conversion will usually require not more than 24 h.

According to one embodiment of the invention the slurry process is performed in the presence of co-crystals of metazachlor and pendimethalin as seeding crystals. Usually 0.01 to 10% by weight, preferably 0.1 to 5% and more preferably 0.3 to 2% by weight of seeding crystals are employed based on the combined weight of metazachlor and pendimethalin.

In another preferred embodiment of the invention the crystalline complex is prepared by process which comprises combining pendimethalin and metazachlor in an aqueous liquid. Combining pendimethalin and metazachlor in an aqueous liquid may be achieved e.g. by combining an aqueous suspension of pendimethalin with an aqueous suspension of metazachlor, or by adding solid metazachlor to an aqueous suspension of pendimethalin, or by adding pendimethalin to an aqueous suspension of metazachlor or by suspending pendimethalin and metazachlor in an aqueous liquid. Thereby, an aqueous suspension is obtained, which contains metazachlor and pendimethalin as a suspension of solid material in an aqueous liquid. The thus obtained aqueous suspension contains the crystalline complex of pendimethalin and metazachlor in the form of suspended particles and optionally an excess of pendimethalin and/or metazachlor as suspended particles.

Combining pendimethalin and metazachlor in the aqueous liquid is preferably accompanied by applying shear forces to the thus obtained aqueous suspension containing pendimethalin and metazachlor. Applying shear forces usually will accelerate the conversion of metazachlor and pendimethalin into the crystalline complex. This particular preferred embodiment is hereinafter also referred to as "shear process".

Combining pendimethalin and metazachlor in the aqueous liquid and/or applying shear forces to the thus obtained aqueous liquid mixture is preferably performed at a temperature of at least 15° C., frequently at a temperature of at least 20° C., preferably at a temperature of at least 30° C., in particular of at least 35° C., e.g. from 15° C. to 80° C., preferably from 20° C. to 60° C., in particular from 30° C. to 55° C. or from 35° C. to 50° C.

Metazachlor is usually present in the liquid medium as solid particles. However, it is not necessary for pendimethalin to be solid during the process and it might be advantageous if the temperature is close to or above the melting point of pendimethalin. Upon applying shear forces to the liquid mixture at elevated temperatures the formation of the crystalline complex might be accelerated.

In the aqueous liquid, wherein metazachlor and pendimethalin are combined, the main constituent of the liquid medium is water, which may contain up to 20% v/v of a water miscible solvent, in particular a solvent of the groups 1 and/or 8, as main constituent. Apart from that, the aqueous liquid may also contain additives which are usually present in a liquid suspension concentrates.

The aqueous suspension, which is obtained by combining metazachlor and pendimethalin in the aqueous liquid, may contain metazachlor and pendimethalin in an amount from 5 to 70% by weight, in particular from 10 to 60% by weight and more preferably from 15 to 50% by weight, based on the total weight of the thus obtained suspension.

The aqueous suspension, which is obtained by combining metazachlor and pendimethalin in the aqueous liquid, may contain metazachlor and pendimethalin in a relative molar ratio varying from 1:5 to 20:1, preferably from 1:1.2 to 15:1. If one of the components is in excess with regard to the stoichiometry of the crystalline complex, a mixture of the crystalline complex and the compound being in excess will be obtained. For formulation purposes, the presence of an excess of metazachlor or pendimethalin might be acceptable. In particular the presence of an excess of metazachlor does not cause stability problems. However, it is preferred, that the amount of pendimethalin in the aqueous suspension does not exceed more than 20 mol-% by weight, in particular not more than 10 mol-%, based on the amount of metazachlor present in the mixture. Therefore, the present invention relates in particular to aqueous formulations containing the crystalline complex of the present invention, provided that, if one or both of metazachlor and pendimethalin are present in the formulation in non-complexed form, the amount of the non-complexed pendimethalin does not exceed 20 mol-%, in particular 10 mol-% in the formulation.

The liquid medium of the aqueous suspension, which is obtained by combining metazachlor and pendimethalin in the aqueous liquid, may include additives which are usually present in a liquid suspension concentrate. Suitable additives are described hereinafter and include surfactants, in particular anionic or non-ionic emulsifiers, wetting agents and dispersants usually employed in crop protection compositions, furthermore antifoam agents, antifreeze agents, agents for adjusting the pH, stabilizers, anti-caking agents, dyes and biocides (preservatives). Preferably, the liquid medium does not contain viscosity-modifying additives (thickeners). The amount of surfactants will generally be from 0.5 to 20% by weight, in particular from 1 to 15% by weight and particularly preferably from 1 to 10% by weight, based on the total weight of the aqueous suspension. The amount of anti-freeze agents may be up to 10% by weight, in particular up to 20% by weight, e.g. from 0.5 to 20% by weight, in particular from 1 to 10% by weight, based on the total weight of the liquid medium, metazachlor and pendimethalin. Further additives, apart from anti-freeze agents and surfactants, may be present in amounts from 0 to 5% by weight, based on the total weight of the liquid medium, metazachlor and pendimethalin.

The time required for formation of the crystalline complex depends in a manner known per se on the applied shear and the temperature and can be determined by the person skilled in the art in standard experiments. Times in the range of e.g. from 10 min. to 48 hours have been found to be suitable for formation of the crystalline complex in the aqueous suspension containing metazachlor and pendimethalin, although a longer period of time is also conceivable. A shearing time of 0.5 to 24 hours is preferred.

In a preferred embodiment, shear forces are applied to the aqueous suspension of pendimethalin and metazachlor, which is obtained by combining metazachlor and pendimethalin in the aqueous liquid. Shear forces can be applied by suitable techniques, which are capable of providing sufficient shear to bring the particles of metazachlor and pendimethalin into an intimate contact and/or to comminute the particles of the crystalline complex. Suitable techniques include grinding, crushing or milling, in particular by wet grinding or wet milling, including e.g. bead milling or by use of a colloid mill. Suitable shearing devices include in particular ball mills or bead mills, agitator ball mills, circulating mills (agitator ball mills with pin grinding system), disk mills, annular chamber mills, double cone mills, triple roll mills, batch mills, colloid mills, and media mills, such as sand mills. To dissipate the heat energy introduced during the grinding process, the grinding chambers are preferably fitted with cooling systems. Particularly suitable is the ball mill Drais Superflow DCP SF 12 from DRAISWERKE, INC. 40 Whitney Road. Mahwah, N.J. 07430 USA, a Drais Perl Mill PMC from DRAISWERKE, INC., the circulating mill system ZETA from Netzsch-Feinmahltechnik GmbH, the disk mill from Netzsch Feinmahltechnik GmbH, Selb, Germany, the bead mill Eiger Mini 50 from Eiger Machinery, Inc., 888 East Belvidere Rd., Grayslake, Ill. 60030 USA and the bead mill DYNO-Mill KDL from WA Bachofen AG, Switzerland. However, other homogenizers might also be suitable, including high shear stirrers, Ultra-Turrax apparatus, static mixers, e.g. systems having mixing nozzles and other homogenizers such as colloid mills.

In a preferred embodiment of the invention, shear is applied by bead milling. In particular, bead sizes in the range of from 0.05 to 5 mm, more particularly from 0.2 to 2.5 mm, and most particularly from 0.5 to 1.5 mm have been found to be suitable. In general, bead loadings in the range of from 40 to 99%, particularly from 70 to 97%, and more particularly from 65 to 95% may be used.

After having applied sufficient shear forces a suspension of the crystalline complex, optionally in admixture with excess metazachlor and/or pendimethalin, is obtained, wherein 90% by weight of the suspended particles have the particle size of not more than 30 µm, preferably not more than 20 µm, in particular not more than 10 µm especially not more than 5 µm, as determined by dynamic light scattering.

The liquid suspension of the crystalline complex thus obtained can, after or in particular before a formulation with additives, be converted by customary drying methods, in particular by spray-drying or freeze-drying, into powder compositions. Before or during drying, a drying or spray auxiliary may be added. Suitable drying or spray auxiliaries for drying aqueous dispersions are known. These include protective colloids, such as polyvinyl alcohol, in particular polyvinyl alcohol having a degree of hydrolysis of >70%, carboxylated polyvinyl alcohol, phenolsulfonic acid/formaldehyde condensates, phenolsulfonic acid/urea/formaldehyde condensates, naphthalenesulfonic acid/formaldehyde condensates, naphthalenesulfonic acid/formaldehyde/urea condensates, polyvinylpyrrolidone, copolymers of maleic acid (or maleic anhydride) and vinylaromatics such as styrene and ethoxylated derivatives thereof, copolymers of maleic acid or maleic anhydride with $C_2$-$C_{10}$-olefins, such as diisobutene, and ethoxylated derivatives thereof, cationic polymers, for example homo- and copolymers of N-alkyl-N-vinylimidazolinium compounds with N-vinyl lactams and the like, and also inorganic anti-blocking agents (sometimes also termed as anti-caking agents), such as silicic acid, in particular pyrogenic silica, alumina, calcium carbonate and the like. The drying auxiliaries are usually employed in an amount of from 0.1 to 20% by weight, based on the weight of the active compound particles in the liquid pesticide composition of the present invention.

As already mentioned above, the crystalline complex as defined herein are suitable for preparing crop protection compositions and in particular for preparing aqueous suspension concentrates. Accordingly, the invention also provides an agricultural composition for crop protection, comprising a crystalline complex as defined herein, if appropriate a liquid carrier (=liquid phase) or a solid carrier and/or one or more customary auxiliaries.

Suitable liquid phases/liquid carriers are water, optionally containing minor amounts of water-miscible organic solvents, such as those of groups 1 to 10, and also organic solvents in which pendimethalin and metazachlor have low or no solubility, for example those in which the solubilities of pendimethalin and metazachlor at 25° C. and 1013 mbar are not more than 1% by weight, in particular not more than 0.1% by weight and especially not more than 0.01% by weight.

Suitable solid carriers are, in principle, all solid substances usually used in crop protection compositions, in particular in fungicides. Solid carriers are, for example, mineral earths, such as silica gels, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Typical auxiliaries comprise surfactants, in particular the wetting agents and dispersants usually employed in crop protection compositions, furthermore viscosity-modifying additives (thickeners), antifoam agents, antifreeze agents, agents for adjusting the pH, stabilizers, anticaking agents and biocides (preservatives).

In particular, the invention relates i to compositions for crop protection in the form of suspension concentrate, in particular an aqueous suspension concentrate (SC). Such suspension concentrates comprise the crystalline complex in a finely divided particulate form, and a liquid carrier (=liquid medium/phase), in particular an aqueous carrier (=aqueous medium/phase), where the particles of the crystalline complex are suspended in the liquid carrier, preferably in the aqueous carrier. The size of the active compound particles, i.e. the size which is not exceeded by 90% by weight of the active compound particles, is typically not more than 30 µm, preferably not more than 20 µm, in particular not more than 10 µm, especially not more than 5 µm, as determined by dynamic light scattering. Advantageously, at least 40% by weight and in particular at least 60% by weight of the particles in the SCs according to the invention have diameters below 2 µm.

Suspension concentrates, in particular aqueous suspension concentrates, can be prepared by suspending the crystalline complex in a suitable liquid carrier, which may contain conventional formulation additives as described hereinafter, where appropriate followed by a comminution of the suspended actives, e.g. by grinding or milling. However, it is preferred to prepare the suspension concentrate by the shear process as described herein, i.e. by applying shear forces to a liquid which contains suspended particles of metazachlor and pendimethalin and optionally further additives until the crystalline complex has been formed.

In addition to the crystalline complex, suspension concentrates typically comprise surfactants, and also, if appropriate, antifoam agents, thickeners, antifreeze agents, stabilizers (biocides), agents for adjusting the pH, anticaking agents and potentially further active compounds.

In such SCs, the amount of active compound, i.e. the total amount of the crystalline complex and, if appropriate, further active compounds is usually in the range from 10 to 70% by weight, in particular in the range from 15 to 50% by weight, based on the total weight of the suspension concentrate.

Preferred surfactants are anionic and non-ionic surfactants (emulsifiers). Suitable surfactants are also protective colloids. The amount of surfactants will generally be from 0.5 to 20% by weight, in particular from 1 to 15% by weight and particularly preferably from 1 to 10% by weight, based on the total weight of the SCs according to the invention. Preferably, the surfactants comprise at least one anionic surfactant and at least one non-ionic surfactant, the ratio of anionic to non-ionic surfactant typically being in the range from 10:1 to 1:10.

Examples of anionic surfactants (anionic tensides, emulsifiers and dispersants) include alkylaryl sulfonates, phenyl sulfonates, alkyl sulfates, alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, alkyl phosphates, alkylaryl phosphates, for example tristyryl phosphates, and the alkali metal, alkaline earth metal, ammonium and amine salts of the substances mentioned above. Preferred anionic surfactants are those which carry at least one sulfonate group, and in particular their alkali metal and their ammonium salts.

Examples of non-ionic surfactants (non-ionic emulsifiers and dispersants) comprise alkylphenol alkoxylates, alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and mixtures thereof. Preferred non-ionic surfactants are fatty alcohol ethoxylates, alkyl polyglycosides, glycerol fatty acid esters, castor oil alkoxylates, fatty acid alkoxylates, fatty amide alkoxylates, lanolin ethoxylates, fatty acid polyglycol esters and ethylene oxide/propylene oxide block copolymers and mixtures thereof.

Protective colloids are typically water soluble, amphiphilic polymers. Examples include proteins and denatured proteins such as casein, polysaccharides such as water soluble starch derivatives and cellulose derivatives, in particular hydrophobic modified starches and celluloses, furthermore polycarboxylates such as polyacrylic acid (polyacrylates), acrylic acid or methacrylic acid copolymers or maleic acid copolymers such as acrylic acid/olefin copolymers, acrylic acid/styrene copolymers, maleic anhydride/olefin copolymers (for example Sokalan® CP9, BASF SE) and the esterification products of said copolymers with polyethylene glycols, polyvinylalcohol, polyvinylpyrrolidone, vinylpyrrolidone copolymers, polyvinylamines, polyethylenimines and polyalkylene ethers.

In particular, the SCs according to the invention comprise at least one surfactant which improves wetting of the plant parts by the aqueous application form (wetting agent) and at least one surfactant which stabilizes the dispersion of the active compound particles in the SC (dispersant). The amount of wetting agent is typically in the range from 0.5 to 10% by weight, in particular from 0.5 to 5% by weight and especially from 0.5 to 3% by weight, based on the total weight of the SC. The amount of dispersant is typically from 0.5 to 10% by weight and in particular from 0.5 to 5% by weight, based on the total weight of the SC.

Preferred wetting agents are of anionic or non-ionic nature and selected, for example, from naphthalenesulfonic acids including their alkali metal, alkaline earth metal, ammonium and amine salts, furthermore fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters.

Preferred dispersants are of anionic or non-ionic nature and selected, for example, from polyethylene glycol/polypropylene glycol block copolymers, polyethylene glycol alkyl ethers, polypropylene glycol alkyl ethers, polyethylene glycol/polypropylene glycol ether block copolymers, alkylaryl phosphates, for example tristyryl phosphates, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/olefin copolymers (for example Sokalan® CP9, BASF SE), including the alkali metal, alkaline earth metal, ammonium and amine salts of the substances mentioned above.

Viscosity-modifying additives (thickeners) suitable for the SCs according to the invention are in particular compounds which bestow upon the formulation pseudoplastic flow properties, i.e. high viscosity in the resting state and low viscosity in the agitated state. Suitable are, in principle, all compounds used for this purpose in suspension concentrates. Mention may be made, for example, of inorganic substances, such as bentonites or attapulgites (for example Attaclay® from Engelhardt), and organic substances, such as polysaccharides and heteropolysaccharides, such as Xanthan Gum® (Kelzan® from Kelco), Rhodopol® 23 (Rhone Poulenc) or Veegum® (from R.T. Vanderbilt), and preference is given to using Xanthan-Gum®. Frequently, the amount of viscosity-modifying additives is from 0.1 to 5% by weight, based on the total weight of the SC.

Antifoam agents suitable for the SCs according to the invention are, for example, silicone emulsions known for this purpose (Silikon® SRE, from Wacker, or Rhodorsil® from Rhodia), long-chain alcohols, fatty acids, defoamers of the type of aqueous wax dispersions, solid defoamers (so-called Compounds), organofluorine compounds and mixtures thereof. The amount of antifoam agent is typically from 0.1 to 1% by weight, based on the total weight of the SC.

Preservatives may be added for stabilizing the suspension concentrates according to the invention. Suitable preservatives are those based on isothiazolones, for example Proxel® from ICI or Acticide® RS from Thor Chemie or Kathon® MK from Rohm & Haas. The amount of bactericides is typically from 0.05 to 0.5% by weight, based on the total weight of the SC.

Suitable antifreeze agents are liquid polyols, for example ethylene glycol, propylene glycol or glycerol. The amount of antifreeze agents is generally from 1 to 20% by weight, in particular from 5 to 10% by weight, based on the total weight of the suspension concentrate.

If appropriate, the SCs according to the invention may comprise buffers for regulating the pH. Examples of buffers are alkali metal salts of weak inorganic or organic acids, such as, for example, phosphoric acid, boric acid, acetic acid, propionic acid, citric acid, fumaric acid, tartaric acid, oxalic acid and succinic acid.

If the formulations of the crystalline complexes are used for seed treatment, they may comprise further customary components as employed in the seed treatment, e.g. in dressing or coating. Examples are in particular colorants, stickers, fillers, and plasticizers besides the above-mentioned components.

Colorants are all dyes and pigments which are customary for such purposes. In this context, both pigments, which are sparingly soluble in water, and dyes, which are soluble in water, may be used. Examples which may be mentioned are the dyes and pigments known under the names Rhodamin B, C. I. Pigment Red 112 and C. I. Solvent Red 1, Pigment blue 15:4, Pigment blue 15:3, Pigment blue 15:2, Pigment blue 15:1, Pigment blue 80, Pigment yellow 1, Pigment yellow 13, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108. The amount of colorants will usually not exceed 20% by weight of the formulation and preferably ranges from 0.1 to 15% by weight, based on the total weight of the formulation.

Stickers are all customary binders which can be employed in dressing products. Examples of suitable binders comprise thermoplastic polymers such as polyvinylpyrrolidone, polyvinyl acetate, polyvinyl alcohol and tylose, furthermore polyacrylates, polymethacrylates, polybutenes, polyisobutenes, polystyrene, polyethylenamines, polyethylenamides, the aforementioned protective colloids, polyesters, polyetheresters, polyanhydrides, polyesterurethanes, polyesteramides, thermoplastic polysaccharides, e.g. cellulose derivates such as celluloseesters, celluloseethers, celluloseetheresters including methylcellulose, ethylcellullose, hydroxymethylcellulose, carboxymethylcellulose, hydroxypropylcellulose and starch derivatives and modified starches, dextrines, maltodextrines, alginates and chitosanes, moreover fats, oils, proteins, including casein, gelatin and zeins, gum arabics, shellacs. Preferred stickers are biocompatible, i.e. they do not have a noticeable phytotoxic activity. Preferably the stickers are biodegradable. Preferably the sticker is chosen that it acts as a matrix for the active ingredients of the formulation. The amount of stickers will usually not exceed 40% by weight of the formulation and preferably ranges from 1 to 40% by weight, and in particular in the range from 5 to 30% by weight, based on the total weight of the formulation.

Besides the sticker the formulation may also contain inert fillers. Examples for these include the aforementioned solid carrier materials, especially fine particulate inorganic materials such as clays, chalk, bentonite, caolin, talc, perlite, mica, silica, diatomaceous earth, quartz powder, montmorillonite, but also fine particulate organic materials such as wood flours, cereal flours, activated carbon and the like. The amount of filler is preferably chosen that the total amount of filler does not exceed 75% by weight, based on the total weight of all non-volatile components of the formulation. Commonly, the amount of filler ranges from 1 to 50% by weight, based on the total weight of all non-volatile components of the formulation.

Besides, the formulation may also contain a plasticizer, which increases the flexibility of the coating. Examples of plasticizers include oligomeric polyalkylenglycoles, glycerol, dialkyl phthalates, alkylbenzyl phthalates, glycol benzoates and related compounds. The amount of plasticizer in the coating frequently ranges from 0.1 to 20% by weight, based on the total weight of the formulation.

The crystalline complexes of the invention can be used in a manner known per se for combating/controlling undesired vegetation. In particular, the crystalline complexes can be formulated together with further active compounds, to increase the activity and/or to widen the activity spectrum. Thus, it may be beneficial to apply them in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added. If applied in combination, the crystalline complexes of the invention are preferably applied together with herbicides and other pesticides which are typically used together with pendimethalin.

Accordingly, a preferred embodiment of the invention relates to an agricultural composition, which, in addition to the crystalline complex, comprises at least one further active compound. Preferably the agricultural composition is in the form of a suspension concentrate comprising, besides the crystalline complex of the invention, the at least one further active compound as finely divided particles.

In principle, the formulations of the crystalline complexes according to the present invention can be used for combating undesired vegetation and all plant diseases caused by harmful fungi or other pests, which can be combated with conventional formulations of pendimethalin and combinations thereof with additional pesticidal agents.

The formulations of the present invention are generally suitable for controlling a large number of harmful plants, including monocotyledonous weeds, in particular annual weeds such as gramineous weeds (grasses) including *Echinochloa* species such as barnyardgrass (*Echinochloa crusgalli* var. *crus-galli*), *Digitaria* species such as crabgrass (*Digitaria sanguinalis*), *Setaria* species such as green foxtail (*Setaria viridis*) and giant foxtail (*Setaria faberii*), *Sorghum* species such as johnsongrass (*Sorghum halepense* Pers.), *Avena* species such as wild oats (*Avena fatua*), *Cenchrus* species such as *Cenchrus echinatus*, *Bromus* species, *Lolium* species, *Phalaris* species, *Eriochloa* species, *Panicum* species, *Brachiaria* species, annual bluegrass (*Poa annua*), blackgrass (*Alopecurus myosuroides*), *Aegilops cylindrica*, *Agropyron repens, Apera spicaventi, Eleusine indica, Cynodon dactylon* and the like.

The formulations are also suitable for controlling a large number of dicotyledonous weeds, in particular broad leaf weeds including *Polygonum* species such as wild buckwheat (*Polygonum convolvolus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, *Cassia* species, *Commelina* species, *Datura* species, *Euphorbia* species, *Geranium* species, *Galinsoga* species, morningglory (*Ipomoea* species), *Lamium* species, *Malva* species, *Matricaria* species, *Sysimbrium* species, *Solanum* species, *Xanthium* species, *Veronica* species, *Viola* species, common chickweed (*Stellaria media*), velvetleaf (*Abutilon theophrasti*), Hemp *sesbania* (*Sesbania exaltata* Cory), *Anoda cristata, Bidens pilosa, Brassica kaber, Capsella bursa-pastoris, Centaurea cyanus, Galeopsis tetrahit, Galium aparine, Helianthus annuus, Desmodium tortuosum, Kochia scoparia, Mercurialis annua, Myosotis arvensis, Papaver rhoeas, Raphanus raphanistrum, Salsola kali, Sinapis arvensis, Sonchus arvensis, Thlaspi arvense, Tagetes minuta, Richardia brasiliensis*, and the like.

The formulations are also suitable for controlling a large number of annual and perennial sedge weeds including *cyperus* species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

The formulations of the invention are particularly suitable for controlling mono- and dicotyledonous weeds and sedge weeds, in particular *Alopecurus myosuroides, Apera spicaventi, Avena fatua, Brachiaria* spec., *Bromus* spec., *Cenchrus* spec., *Digitaria* spec., *Echinochloa* spec., *Eleusine indica, Eriochloa* spec., *Geranium* spec., *Lolium* spec., *Panicum* spec., *Phalaris* spec., *Poa annua, Setaria* spec., *Sorghum* spec., *Abuthilon theoprasti, Amaranthus* spec., *Anthemis* spec., *Atriplex* spec., *Brassica kaber, Capsella bursa-pastoris, Chenopodium* spec., *Conyza* spec., *Euphorbia* spec., *Galium aparine, Kochia scoparia, Lamium* spec., *Matricaria* spec., *Papaver rhoeas, Polygonum* spec., *Raphanus raphanistrum, Sinapis arvensis, Stellaria media, Solanum* spec., *Sysimbrium* spec., *Thlaspi arvense, Veronica* spec., *Viola* spec., *Commelina* spec. and *Cyperus* spec.

The formulations according to the present invention are suitable for combating/controlling common harmful plants in useful plants (i.e. in crops). They are generally suitable for combating/controlling undesired vegetation in Grain crops, including e.g.
cereals such as wheat (*Triticum aestivum*) and wheat like crops such as durum (*T. durum*), einkorn (*T. monococcum*), emmer (*T. dicoccon*) and spelt (*T. spelta*), rye (*Secale cereale*), triticale (*Tritiosecale*), barley (*Hordeum vulgare*);
maize (corn; *Zea mays*);
sorghum (e.g. *Sorghum bicolour*);
rice (*Oryza* spp. such as *Oryza sativa* and *Oryza glaberrima*); and
sugar cane;

Legumes (Fabaceae), including e.g. soybeans (*Glycine max.*), peanuts (*Arachis hypogaea* and pulse crops such as peas including *Pisum sativum*, pigeon pea and cowpea, beans including broad beans (*Vicia faba*), *Vigna* spp., and *Phaseolus* spp. and lentils (*lens culinaris* var.);

brassicaceae, including e.g. canola (*Brassica napus*), oilseed rape (*Brassica napus*), cabbage (*B. oleracea* var.), mustard such as *B. juncea, B. campestris, B. narinosa, B. nigra* and *B. tournefortii*; and turnip (*Brassica raga* var.);

other broadleaf crops including e.g. sunflower, cotton, flax, linseed, sugarbeet, potato and tomato;

TNV-crops (TNV: trees, nuts and vine) including e.g. grapes, citrus, pomefruit, e.g. apple and pear, coffee, pistachio and oilpalm, stonefruit, e.g. peach, almond, walnut, olive, cherry, plum and apricot;

turf, pasture and rangeland;

onion and garlic;

bulb ornamentals such as tulips and narcissus;

conifers and deciduous trees such as *pinus*, fir, oak, maple, dogwood, hawthorne, crabapple, and *rhamnus* (buckthorn); and garden ornamentals such as petunia, marigold, roses and snapdragon.

The compositions of the invention are in particular suitable for combating undesired vegetation in wheat, barley, rye, triticale, durum, rice, corn, sugarcane, sorghum, soybean, pulse crops such as pea, bean and lentils, peanut, sunflower, sugarbeet, potato, cotton, *brassica* crops, such as oilseed rape, canola, mustard, cabbage and turnip, turf, grapes, stonefruit, such as peach, almond, walnut, olive, cherry, plum and apricot, citrus and pistachio.

The compositions according to the invention can also be used in crop plants which are resistant to one or more herbicides owing to genetic engineering or breeding, which are resistant to one or more pathogens such as fungi owing to genetic engineering or breeding, or which are resistant to attack by insects owing to genetic engineering or breeding. Suitable are for example crop plants, preferably corn, wheat, sunflower, rice, canola, oilseed rape, soybeans or lentils which are resistant to, for example, pendimethalin, or crop plants which, owing to introduction of the gene for Bt toxin by genetic modification, are resistant to attack by certain insects.

The compositions of the present invention can be applied in conventional manner by using techniques as skilled person is familiar with. Suitable techniques include spraying, atomizing, spreading or watering. The type of application depends on the intended purpose in a well known manner; in any case, they should ensure the finest possible distribution of the active ingredients according to the invention.

The compositions can be applied pre- or post-emergence, i.e. before, during and/or after emergence of the undesirable plants. When the compositions are used in crops, they can be applied after seeding and before or after the emergence of the crop plants. The compositions invention can, however, also be applied prior to seeding of the crop plants.

The compositions are applied to the plants mainly by spraying, in particular soil and foliar spraying. Application can be carried out by customary spraying techniques using, for example, water as carrier and spray liquor rates of from about 10 to 2000 l/ha or 50 to 1000 l/ha (for example from 100 to 500 l/ha). Application of the compositions by the low-volume and the ultra-low-volume method is possible.

If the active ingredients are less well tolerated by certain crop plants, application techniques may be used in which the compositions are sprayed, with the aid of the spray apparatus, in such a way that they come into as little contact, if any, with the leaves of the sensitive crop plants while reaching the leaves of undesirable plants, which grow underneath, or the bare soil (post-directed, lay-by).

In the case of a post-emergence treatment of the plants, the herbicidal mixtures or compositions according to the invention are preferably applied by foliar application. Application may be effected, for example, by usual spraying techniques with water as the carrier, using amounts of spray mixture of approx. 50 to 1000 l/ha.

The required application rate of the composition of the pure active compounds, i.e. of pendimethalin, metazachlor and optionally further active compounds depends on the density of the undesired vegetation, on the development stage of the plants, on the climatic conditions of the location where the composition is used and on the application method. In general, the application rate of the composition (total amount of pendimethalin, metazachlor and optionally further active compounds) is from 15 to 5000 g/ha, preferably from 20 to 2500 g/ha of active substance.

The complexes of to the present invention may be formulated with further compounds showing an activity against undesired vegetation, phytopathogenic fungi or other pests in a manner known per se. In this respect it has proven to be particularly advantageous to formulate a crystalline complex together with at least one further active ingredient which is also active against undesired vegetation.

Accordingly one embodiment of the invention relates to a formulation comprising a crystalline complex of pendimethalin and metazachlor of the invention that is formulated with one or more imidazolinone herbicides. Imidazolinone herbicides are known e.g. from Shaner, D. L. O'Conner, S. L The Imidazolinone Herbicides, CRC Press Inc., Boca Raton, Fla. 1991 and also from The Compendium of Pesticide Common Names http://www.alanwood.net/pesticides/. Preferred imidazolinone herbicides include imazamox, imazapic, imazapyr, imazaquin, imazethapyr, their salts and their esters, as well as mixtures thereof.

In this embodiment the relative weight ratio of pendimethalin and the imidazolinone herbicide is preferably from 1:200 to 200:1, in particular in the range from 1:50 to 50:1 and more preferably from 1:10 to 10:1.

The novel crystalline complexes allow the preparation of low-solvent or solvent-free aqueous suspension concentrates both of the crystalline complex on its own and of the crystalline complexes with further crop protection agents, in particular the mixing partners indicated above. The solvent content, in particular the content of aromatic hydrocarbons, minus any antifreeze agents, is generally not more than 2% by weight of the suspension concentrate and is frequently below 2% by weight. The suspension concentrates according to the invention are distinguished in particular by better storage stability compared to the known suspension concentrates and suspoemulsion concentrates containing pendimethalin or a mixture of pendimethalin and metazachlor.

The figures and examples below serve to illustrate the invention and are not to be understood as limiting it.

ANALYSIS

The picture of the X-ray powder diffractogram (PXRD) was taken using a D-5000 diffractometer from Siemens with a Cu anode (λ=1.5406 Å; 45 kV, 25 mA) in reflection geometry in the range from 2θ=4°-35° with increments of 0.02° at 25° C. The 2θ values found were used to calculate the stated interplanar spacing d.

Single crystal X-ray diffraction. The data were collected at 103(2) K on a Bruker AXS CCD Detector, using graphite-monochromated CuKα radiation (λ=1.54178 Å). The structure was solved with direct methods, refined, and expanded by using Fourier techniques with the SHELX-97 software package.

Thermogravimetric/differential thermal analyses (TG/DTA) were carried out with a Mettler Toledo TGA/SDTA 851 using $Al_2O_3$ as reference. The samples (8-22 mg) were placed in platinum sample cups for measurement. A temperature program from 30 to 605° C. at 10° C./min and nitrogen gas flow was used.

Differential scanning calorimetric determinations (DSC) were made on a Mettler Toledo DSC 823e with TS0801RO Sample Robot and TS08006C1 Gas Control. The measurements were done with heating rates 5° C./min from 30 to 185° C. using aluminum crucibles with pinholes.

PREPARATION EXAMPLES

Figure 1:
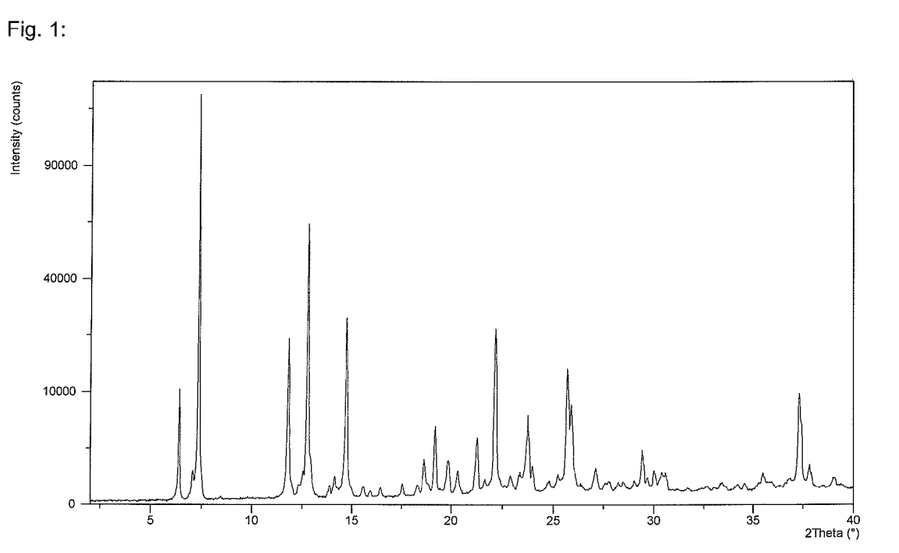
FIG. 1: X-ray powder diffractogram of the co-crystal of metazachlor and pendimethalin.
Figure 2:
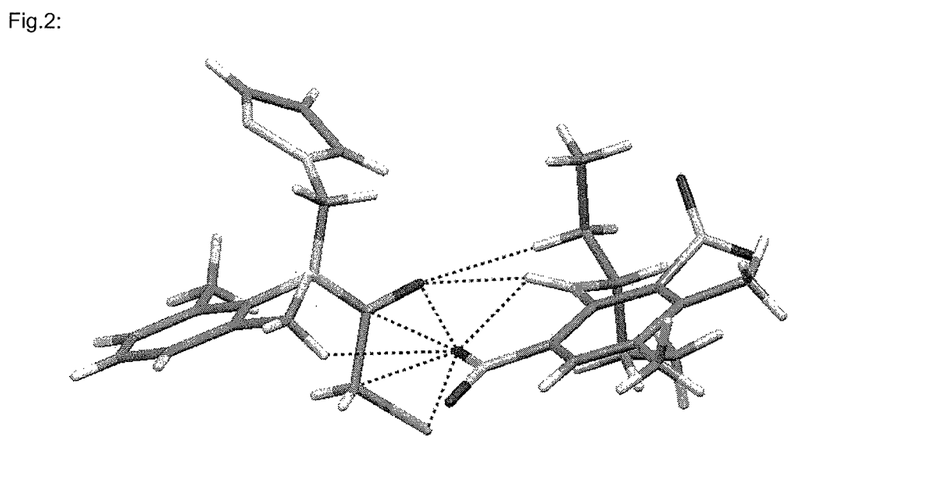
FIG. 2: Asymmetric unit of the crystal structure of the co-crystal of metazachlor (left) and pendimethalin (right) according to X-ray analysis of single crystals, with non-carbon and non-hydrogen atoms indicated.
Figure 3:
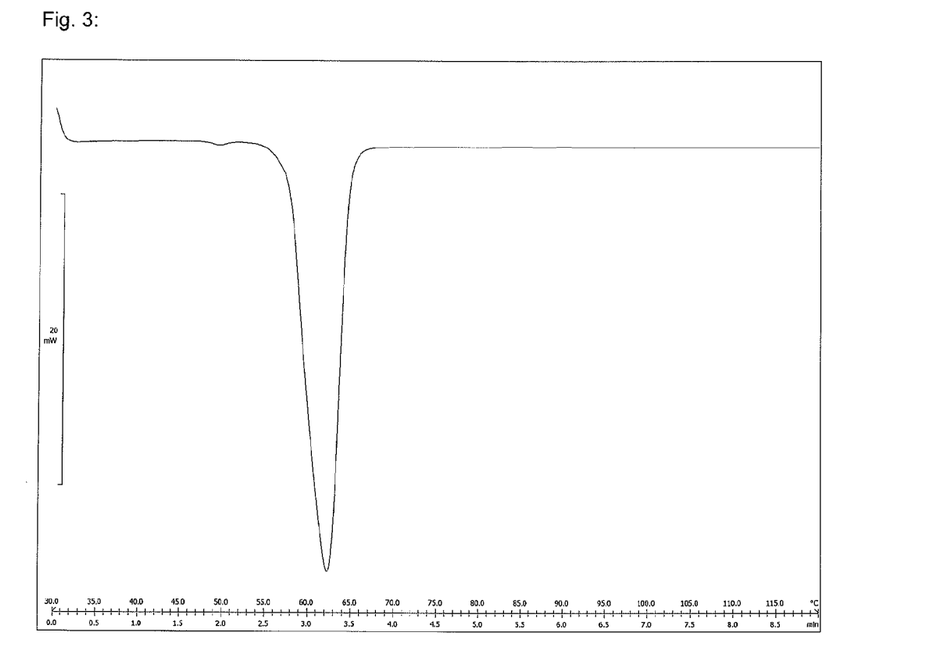
FIG. 3: DSC trace of the co-crystal of metazachlor and pendimethalin showing an endothermic melting peak with an onset at 57° C. and peak maximum at about 62° C.; heating rate 10° C./min.
Figure 4:
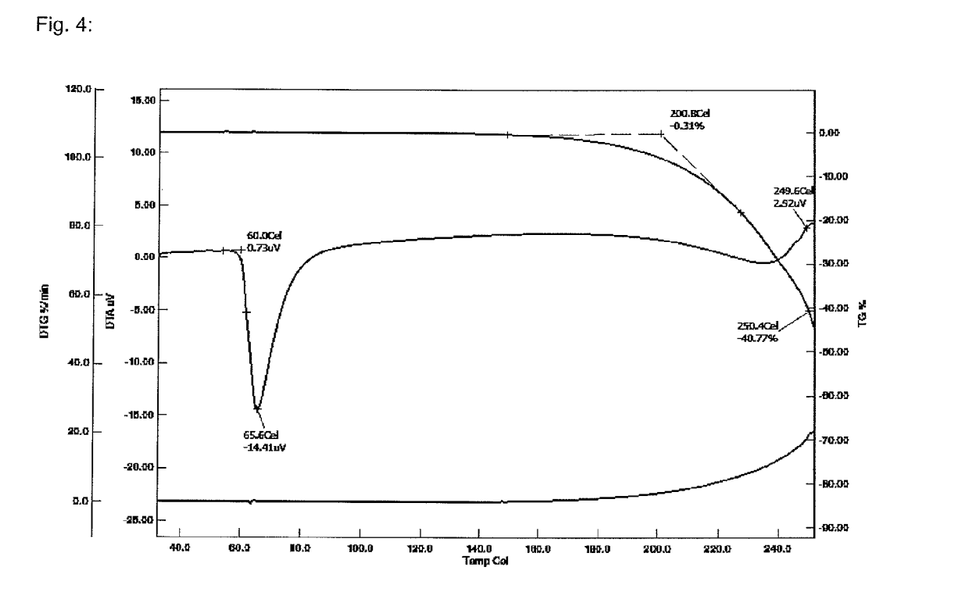
FIG. 4: TGA thermogram of the co-crystal of metazachlor and pendimethalin.

I Slurry Process 498 mg pendimethalin and 493 mg metazachlor (1:1 molar ratio) were given in a flask together with 20 ml of a mixture of water and ethanol (19:1 v/v). After stirring at 40° C. for 30 minutes approximately 5-10 mg co-crystals of metazachlor and pendimethalin were added as seeding crystals. The mixture was stirred for 5 days, after which it was cooled down to 23° C., filtered and left to dry for 16 h at 23° C. on a clay plate. An PXRD revealed that the obtained crystalline material was a co-crystal of metazachlor and pendimethalin with the characteristic PXRD pattern shown in FIG. 1. Melting of the crystalline complex began at 57° C.

II Shear Process

The following formulation additives were used:
A sample of 5 kg was prepared according to the recipe given in the following table (all amounts are given in g/kg). All components except the aqueous xanthan gum solution and disperse green were mixed in a vessel and then milled by two consecutive passes at 8 kg/h through a 600-ml bead-mill ran at a tip-speed of 6.7 m/s, while keeping the mixture at 20° C. To the obtained mixture the 2% solution of xanthan gum and the dye formulation were given with stirring. A homogeneous slightly viscous green opaque liquid was obtained. The particle size of this dispersion was determined by laser-diffraction on a 100-fold dilution in water to show 90% of the particles to have a size below 3.9 μm ($D_{90}$ value).

A sample was evaporated to dryness. A PXRD of the obtained material revealed the presence of the crystalline complex of pendimethalin and metazachlor besides excess metazachlor.

| | |
|---|---|
| Pendimethalin | 42 |
| Metazachlor | 378 |
| Glycerol | 70 |
| Dispersant 1 | 30 |
| Dispersant 2 | 19 |
| Dispersant 3 | 6 |
| Defoamer | 5 |
| Xanthan Gum (2% solution in water) | 55 |
| Dye formulation | 100 |
| water | 295 |

Dispersant 1: Ethylene oxide/propylene oxide block copolymer (Pluronic PE 10500 of BASF SE).
Dispersant 2: Acrylic graft copolymer (Atlox 4913 of Uniquema).
Dispersant 3: Ethoxylated tristyrylphenol ammonium sulfate having 16 oxyethylene units: Soprophor 4D384 of Rhodia.
Dispersant 4: Sodium salt of the condensation product of phenolsulfonic acid and formaldehyde.
Defoamer: Commercial silicon defoamer (aqueous emulsion, 20% by weight of actives - Silfoam SRE obtained from Wacker Chemie AG.
Dye-formulation: Disperse Green Storage Stability:

The stability of the pendimethalin/metazachlor co-crystal as produced according to the aforementioned example was determined by stirring a 1 g sample in 20 ml water at RT for two weeks. Afterwards it was verified by hot stage microscopy and PXRD that no transformation to any other crystal modification took place.

We claim:

1. A crystalline complex comprising pendimethalin and metazachlor, wherein the molar ratio of metazachlor and pendimethalin is from 0.8:1 to 1.25:1.

2. A crystalline complex comprising pendimethalin and metazachlor, which, in an X-ray powder diffractogram at 25° C. and Cu radiation, shows at least four of the following reflexes, given as 2θ values: 6.40±0.2°, 7.06±0.2°, 7.36±0.2°, 11.82±0.2°, 12.78±0.2°, 14.72±0.2°, 19.21±0.2°, 21.28±0.2°, 22.15±0.2°.

3. A process for preparing the crystalline complex as defined in claim 1, which comprises suspending pendimethalin and metazachlor in an organic solvent or in a mixture of water and an organic solvent.

4. A process for preparing the crystalline complex as defined in according to claim 1, wherein shear forces are applied to an aqueous suspension containing pendimethalin and metazachlor, which is obtained by combining pendimethalin and metazachlor in the aqueous liquid.

5. An agricultural composition comprising a crystalline complex of pendimethalin and metazachlor as defined in claim 1.

6. The agricultural composition according to claim 5, containing the crystalline complex of pendimethalin and metazachlor in the form of an aqueous suspension.

7. The agricultural composition according to claim 5, containing an additional active compound.

8. The agricultural composition according to claim 7, wherein the additional active compound is an imidazolinone herbicide.

9. The agricultural composition of claim 8, wherein the molar ratio of metazachlor and pendimethalin is from 0.8:1 to 1.25:1.

10. The crystalline complex of claim 1, which, in an X-ray powder diffractogram at 25° C. and Cu radiation, shows at least four of the following reflexes, given as 2θ values: 6.40±0.2°, 7.06±0.2°, 7.36±0.2°, 11.82±0.2°, 12.78±0.2°, 14.72±0.2°, 19.21±0.2°, 21.28±0.2°, 22.15±0.2°.

11. A process for preparing the crystalline complex as defined in claim 2, which comprises suspending pendimethalin and metazachlor in an organic solvent or in a mixture of water and an organic solvent.

12. The process according to claim 2, wherein shear forces are applied to an aqueous suspension containing pendimethalin and metazachlor, which is obtained by combining pendimethalin and metazachlor in the aqueous liquid.

13. An agricultural composition comprising a crystalline complex of pendimethalin and metazachlor as defined in claim 2.

14. The agricultural composition according to claim 13, containing the crystalline complex of pendimethalin and metazachlor in the form of an aqueous suspension.

15. The agricultural composition according to claim 13, containing an additional active compound.

16. The composition according to claim 15, wherein the additional active compound is an imidazolinone herbicide.

* * * * *